(12) United States Patent
Lidgren

(10) Patent No.: US 8,586,101 B2
(45) Date of Patent: *Nov. 19, 2013

(54) BIORESORBABLE BONE MINERAL SUBSTITUTE COMPRISING WATER-SOLUBLE X-RAY CONTRAST AGENT

(75) Inventor: Lars Lidgren, Lund (SE)

(73) Assignee: Bone Support AB, Lund (SE)

( * ) Notice: Subject to any disclaimer, the term of this patent is extended or adjusted under 35 U.S.C. 154(b) by 1561 days.

This patent is subject to a terminal disclaimer.

(21) Appl. No.: 10/499,023

(22) PCT Filed: Dec. 20, 2002

(86) PCT No.: PCT/SE02/02428
§ 371 (c)(1),
(2), (4) Date: Feb. 8, 2005

(87) PCT Pub. No.: WO03/053488
PCT Pub. Date: Jul. 3, 2003

(65) Prior Publication Data
US 2005/0119746 A1    Jun. 2, 2005

Related U.S. Application Data

(60) Provisional application No. 60/341,282, filed on Dec. 20, 2001.

(30) Foreign Application Priority Data

Dec. 20, 2001  (SE) .................................. 0104359

(51) Int. Cl.
A61K 33/42    (2006.01)
A61F 2/02     (2006.01)
A61F 2/28     (2006.01)

(52) U.S. Cl.
USPC ........... 424/602; 424/426; 523/115; 523/116; 523/117; 623/16.11; 623/23.61; 623/23.62

(58) Field of Classification Search
USPC ......................................... 424/9.4; 623/16.11
See application file for complete search history.

(56) References Cited

U.S. PATENT DOCUMENTS

| | | |
|---|---|---|
| 949,463 A | 2/1910 | Stapley |
| 1,644,173 A | 10/1927 | Carr |
| 1,865,912 A | 7/1932 | Horn |
| 2,545,017 A | 3/1951 | Billingsley |
| 3,367,783 A | 2/1968 | Billerbeck |
| 3,688,765 A | 9/1972 | Gasaway |
| 3,837,379 A | 9/1974 | McDonald et al. |
| 3,965,910 A | 6/1976 | Fischer |
| 4,001,323 A | 1/1977 | Felder et al. |
| 4,139,605 A | 2/1979 | Felder et al. |
| 4,240,425 A | 12/1980 | Akhavi |
| 4,269,331 A | 5/1981 | Watson |
| 4,348,377 A | 9/1982 | Felder et al. |
| 4,487,766 A | 12/1984 | Mach |
| 4,496,342 A | 1/1985 | Banko |
| 4,583,974 A | 4/1986 | Kokernak |
| 4,619,655 A | 10/1986 | Hanker et al. |
| 4,673,296 A | 6/1987 | Sjogren |
| 4,721,390 A | 1/1988 | Lidgren |
| 4,752,479 A | 6/1988 | Briggs et al. |
| 4,832,500 A | 5/1989 | Brunold et al. |
| 4,994,442 A | 2/1991 | Gil et al. |
| 5,047,030 A | 9/1991 | Draenert |
| 5,071,040 A | 12/1991 | Laptewicz, Jr. |
| 5,073,362 A | 12/1991 | Blaszkiewicz et al. |
| 5,149,368 A | 9/1992 | Liu et al. |
| 5,168,757 A | 12/1992 | Rabenau et al. |
| 5,232,024 A | 8/1993 | Williams |
| 5,252,301 A | 10/1993 | Nilson et al. |
| 5,262,166 A | 11/1993 | Liu et al. |
| 5,269,785 A | 12/1993 | Bonutti |
| 5,281,265 A * | 1/1994 | Liu ............................ 106/35 |
| 5,328,262 A | 7/1994 | Lidgren et al. |
| 5,328,462 A | 7/1994 | Fischer |
| 5,342,441 A | 8/1994 | Mandai et al. |
| 5,360,823 A | 11/1994 | Griffel et al. |
| 5,403,318 A | 4/1995 | Boehringer et al. |
| 5,447,711 A | 9/1995 | Almen et al. |
| 5,462,722 A | 10/1995 | Liu et al. |
| 5,549,380 A | 8/1996 | Lidgren et al. |
| 5,605,885 A | 2/1997 | Bernton et al. |
| 5,614,206 A | 3/1997 | Randolph et al. |
| 5,650,108 A | 7/1997 | Nieset et al. |
| 5,665,066 A | 9/1997 | Fischer |
| 5,681,873 A | 10/1997 | Norton et al. |
| 5,695,742 A | 12/1997 | Felder et al. |
| 5,797,873 A | 8/1998 | Franz et al. |
| 5,837,752 A | 11/1998 | Shastri et al. |
| 5,842,786 A | 12/1998 | Solomon |
| 5,866,100 A | 2/1999 | Tournier et al. |
| 5,871,549 A | 2/1999 | Jayashankar et al. |
| 5,965,772 A | 10/1999 | Desantis |
| 5,997,544 A | 12/1999 | Nies et al. |
| 6,018,094 A | 1/2000 | Fox |
| 6,018,095 A | 1/2000 | Lerch et al. |

(Continued)

FOREIGN PATENT DOCUMENTS

| | | |
|---|---|---|
| DE | 44 09 610 A1 | 9/1995 |
| DE | 202 16 632 | 3/2004 |

(Continued)

OTHER PUBLICATIONS

Komath et al., "On the development of an apatite calcium phosphate bone cement," 2000, Bull. Mater. Sci., vol. 23, No. 2, pp. 135-140.*

(Continued)

Primary Examiner — Kevin S Orwig
(74) Attorney, Agent, or Firm — Finnegan, Henderson, Farabow, Garrett & Dunner, LLP

(57) ABSTRACT

The invention refers to an artificial bone mineral substitute material which comprises at least one ceramic and at least one water soluble non-ionic X-ray contrast agent. The invention refers to a composition for producing the same, which further comprises an aqueous liquid, as well as the use of the composition as a X-ray contrast medium.

10 Claims, 2 Drawing Sheets

(56) References Cited

U.S. PATENT DOCUMENTS

| | | | |
|---|---|---|---|
| 6,062,722 | A | 5/2000 | Lake |
| 6,071,982 | A | 6/2000 | Wise et al. |
| 6,074,358 | A | 6/2000 | Andrew et al. |
| 6,075,067 | A | 6/2000 | Lidgren |
| 6,080,801 | A | 6/2000 | Draenert et al. |
| 6,118,043 | A | 9/2000 | Nies et al. |
| 6,120,174 | A | 9/2000 | Hoag et al. |
| 6,206,957 | B1 | 3/2001 | Driessens et al. |
| 6,231,615 | B1 | 5/2001 | Preissman |
| 6,248,110 | B1 | 6/2001 | Reiley et al. |
| 6,251,139 | B1 | 6/2001 | Lin et al. |
| 6,309,420 | B1 | 10/2001 | Preissman |
| 6,365,218 | B1 | 4/2002 | Borschel et al. |
| 6,440,138 | B1 | 8/2002 | Reiley et al. |
| 6,447,809 | B1 | 9/2002 | Krumhar et al. |
| 6,485,428 | B1 | 11/2002 | Enk |
| 6,586,009 | B1 | 7/2003 | Lidgren |
| 6,596,904 | B1 | 7/2003 | Dunn et al. |
| 6,689,375 | B1 | 2/2004 | Wahlig et al. |
| 6,706,069 | B2 * | 3/2004 | Berger .................. 623/17.12 |
| 6,706,273 | B1 | 3/2004 | Roessler |
| 6,716,216 | B1 | 4/2004 | Boucher et al. |
| 6,719,761 | B1 | 4/2004 | Reiley et al. |
| 6,723,334 | B1 * | 4/2004 | McGee et al. .................. 523/116 |
| 6,740,090 | B1 | 5/2004 | Cragg et al. |
| 6,897,339 | B2 | 5/2005 | Turchetta et al. |
| 7,160,306 | B2 | 1/2007 | Matsuzaki et al. |
| 7,393,342 | B2 | 7/2008 | Henniges et al. |
| 7,417,077 | B2 | 8/2008 | Lidgren et al. |
| 7,524,103 | B2 | 4/2009 | McGill et al. |
| 7,972,630 | B2 | 7/2011 | Lidgren |
| 2001/0012968 | A1 * | 8/2001 | Preissman .................. 623/23.73 |
| 2001/0051670 | A1 | 12/2001 | Goupil et al. |
| 2002/0055143 | A1 | 5/2002 | Bell et al. |
| 2002/0076378 | A1 | 6/2002 | Wolfe et al. |
| 2002/0101785 | A1 | 8/2002 | Edwards et al. |
| 2002/0156483 | A1 | 10/2002 | Voellmicke et al. |
| 2002/0169506 | A1 | 11/2002 | Matsushima et al. |
| 2003/0018339 | A1 | 1/2003 | Higueras et al. |
| 2003/0028251 | A1 | 2/2003 | Matthews |
| 2003/0040718 | A1 | 2/2003 | Kust et al. |
| 2003/0050702 | A1 * | 3/2003 | Berger .................. 623/17.12 |
| 2003/0055512 | A1 | 3/2003 | Genin et al. |
| 2003/0109883 | A1 | 6/2003 | Matsuzaki et al. |
| 2003/0161858 | A1 | 8/2003 | Lidgren |
| 2003/0181986 | A1 | 9/2003 | Buchholz |
| 2004/0006347 | A1 | 1/2004 | Sproul |
| 2004/0048947 | A1 | 3/2004 | Lidgren et al. |
| 2004/0049202 | A1 * | 3/2004 | Berger .................. 606/90 |
| 2004/0068234 | A1 | 4/2004 | Martin et al. |
| 2004/0068266 | A1 | 4/2004 | Delmotte |
| 2004/0151751 | A1 | 8/2004 | Cooper |
| 2004/0191897 | A1 | 9/2004 | Muschler |
| 2004/0244651 | A1 | 12/2004 | Lemaitre et al. |
| 2005/0015074 | A1 | 1/2005 | Trombley, III |
| 2005/0023171 | A1 | 2/2005 | Delaney et al. |
| 2005/0119746 | A1 | 6/2005 | Lidgren |
| 2005/0197629 | A1 | 9/2005 | Conway |
| 2005/0241535 | A1 | 11/2005 | Bohner |
| 2005/0251149 | A1 | 11/2005 | Wenz |
| 2005/0257714 | A1 | 11/2005 | Constanz et al. |
| 2005/0287071 | A1 | 12/2005 | Wenz |
| 2006/0004358 | A1 | 1/2006 | Serhan et al. |
| 2006/0036211 | A1 | 2/2006 | Solsberg et al. |
| 2006/0041033 | A1 | 2/2006 | Bisig et al. |
| 2006/0122621 | A1 | 6/2006 | Truckai et al. |
| 2007/0041906 | A1 * | 2/2007 | Lidgren et al. .................. 424/9.4 |
| 2007/0161943 | A1 * | 7/2007 | Lidgren et al. .................. 604/19 |
| 2008/0065088 | A1 | 3/2008 | Hughes et al. |
| 2008/0161752 | A1 | 7/2008 | Rajala et al. |
| 2008/0318862 | A1 | 12/2008 | Ashman et al. |
| 2010/0008181 | A1 | 1/2010 | Lidgren et al. |
| 2010/0249753 | A1 | 9/2010 | Gaisser et al. |

FOREIGN PATENT DOCUMENTS

| | | | |
|---|---|---|---|
| EP | 0 023 992 | | 2/1981 |
| EP | 0 109 310 | B1 | 5/1984 |
| EP | 0 308 364 | A2 | 3/1989 |
| EP | 0 495 284 | A1 | 7/1992 |
| EP | 0 520 690 | B1 | 12/1992 |
| EP | 0 639 382 | A1 | 2/1995 |
| EP | 0 639 382 | B1 | 2/1995 |
| EP | 0 807 432 | B1 | 11/1997 |
| EP | 0 950 420 | A2 | 10/1999 |
| EP | 1 002 513 | | 5/2000 |
| EP | 1 208 850 | A1 | 5/2002 |
| EP | 1 132 061 | B1 | 8/2004 |
| ES | 2 178 556 | | 12/2002 |
| GB | 2 338 428 | | 12/1999 |
| JP | 64-22256 | A | 1/1989 |
| JP | 64-22257 | A | 1/1989 |
| JP | 1-139516 | | 6/1989 |
| JP | 5-168692 | A | 7/1993 |
| JP | 9-502368 | | 3/1997 |
| JP | 2935708 | | 8/1999 |
| JP | 2000-295 | A | 1/2000 |
| JP | 2000-159564 | | 6/2000 |
| JP | 2001-106638 | A | 4/2001 |
| JP | 2001-510078 | | 7/2001 |
| JP | 2001-517997 | | 10/2001 |
| JP | 2002-58736 | | 2/2002 |
| JP | 2002-325831 | | 11/2002 |
| JP | 2003-507090 | | 2/2003 |
| SE | 8903538 | | 4/1991 |
| WO | WO 85/01727 | | 4/1985 |
| WO | WO 87/05521 | | 9/1987 |
| WO | WO 88/06023 | | 8/1988 |
| WO | WO 89/03695 | | 5/1989 |
| WO | WO 91/00252 | * | 1/1991 .............. A61K 35/14 |
| WO | WO 91/17722 | | 11/1991 |
| WO | WO 93/14799 | | 8/1993 |
| WO | WO 95/07108 | | 3/1995 |
| WO | WO 96/39202 | | 12/1996 |
| WO | WO 91/00252 | | 1/1997 |
| WO | WO 97/38676 | | 10/1997 |
| WO | WO 97/47334 | | 12/1997 |
| WO | WO 99/17710 | | 4/1999 |
| WO | WO 99/62570 | | 12/1999 |
| WO | WO 00/02597 | | 1/2000 |
| WO | WO 00/45867 | | 8/2000 |
| WO | WO 01/34216 | | 5/2001 |
| WO | WO 01/76649 | A1 | 10/2001 |
| WO | WO 02/05861 | | 1/2002 |
| WO | WO 02/05861 | A1 | 1/2002 |
| WO | WO 02/058755 | | 8/2002 |
| WO | WO 02/080933 | | 10/2002 |
| WO | WO 03/037165 | | 5/2003 |
| WO | WO 03/041753 | | 5/2003 |
| WO | WO 03/053488 | | 7/2003 |
| WO | WO 03/053488 | A1 | 7/2003 |
| WO | WO 04/000374 | | 12/2003 |
| WO | WO 2004/078223 | A1 | 9/2004 |
| WO | WO 2005/099783 | A1 | 10/2005 |
| WO | WO 2005/122971 | A1 | 12/2005 |
| WO | WO 2006/041365 | | 4/2006 |

OTHER PUBLICATIONS

Ima-Nirwana et al.,"Palm Vitamin E improves bone metabolism and survival rate in thyroxic rats," 1999, General Pharmacology, vol. 32, pp. 621-626.*

Database WPI: Week 200138, Derwent Publications Ltd., WO 01/34216.

Database WPI: Week 199433, Derwent Publications Ltd., London, GB; AN 1994-269325 & JP 61 99623 A (Lion Corp et al), Jul. 19, 1994.

Apr. 4, 2003, International Search Report.

Mar. 16, 2004, International Preliminary Examination Report.

Database WPI: Week 199734, Derwent Publications Ltd., EP 0 807 432 B1.

International Search Report from PCT/SE01/01627 dated Dec. 18, 2001, related to U.S. Appl. No. 10/333,026.

(56) References Cited

OTHER PUBLICATIONS

International Preliminary Examination Report for PCT/SE01/01627 dated Oct. 14, 2002, related to U.S. Appl. No. 10/333,026.
International Search Report for PCT/SE2004/000328 dated Jun. 8, 2004, related to U.S. Appl. No. 10/547,671.
International Preliminary Examination Report PCT/SE2004/000328 dated Aug. 30, 2005, related to U.S. Appl. No. 10/547,671.
Office Action in copending U.S. Appl. No. 10/333,026 dated Mar. 21, 2006.
Office Action in copending U.S. Appl. No. 10/333,026 dated Oct. 31, 2006.
Bohner, M. et al. "Effects of Sulfate Ions on the in vitro Properties of the β-TCP-MCPM-Water Mixtures. Preliminary in vivo Results," *Ceramic Transactions* (1995) 48, 245-259.
Bohner, M. "New hydraulic cements based on α-tricalcium phosphate-calcium sulfate dihydrate mixtures," *Biomaterials* (2004) 25, 741-749.
Mirtchi, A. A. et al. "Calcium phosphate cements: action of setting regulators on the properties of the β-tricalcium phosphate-monocalcium phosphate cements," *Biomaterials* (1989) 10(9), 634-638.
Nilsson, M. et al. "Characterization of a novel calcium phosphate/sulphate bone cement," *J. Biomedical Materials Research* (2002) 61(4), 600-607.
Nilsson, M. et al. "New Perspectives of Bioactives Calcium Phosphate Cements for Biomedical Applications," *Research Centre in Biomedical Engineering, Dept. of Material Science and Metallurgy*, Universitat Politècnica de Catalunya, Avda, Diagonal 647, Barcelona, E-08028, Spain, pp. 95-99, Nov. 2000.
Database WPI: Week 199126, Derwent Publications Ltd., SE 8903538.
Database WPI: Week 198928, Derwent Publications Ltd., JP 1-139516.
International Preliminary Examination Report for PCT/SE01/00789 dated Jan. 11, 2002, related to U.S. Appl. No. 10/257,561.
International Search Report for PCT/SE01/00789 dated Jul. 9, 2001, related to U.S. Appl. No. 10/257,561.
Cabañas, M. V. "Setting Behavior and in Vitro Bioactivity of Hydroxyapatite/Calcium Sulfate Cements," *Chem. Mater.* (2002) 14, 3550-3555.
Copending U.S. Appl. No. 10/257,561, Office Action dated Mar. 28, 2007.
Copending U.S. Appl. No. 10/257,561, Office Action dated Sep. 5, 2006.
Office Action in copending U.S. Appl. No. 10/333,026 dated Oct. 10, 2007.
Office Action in copending U.S. Appl. No. 10/257,561 dated Oct. 15, 2007.
English-language translation of SE 8903538, "Implant material and method for the manufacture thereof."
English-language translation of JP 1-139516.
Aebli, N. et al., "Cardiovascular Changes During Multiple Vertebroplasty With and Without Vent-Hole," *SPINE* (2003) 28(14):1504-1512.
Engqvist, H. et al., "Chemical Stability of a Novel Injectable Bioceramic for Stabilisation of Vertebral Compression Fractures," *Trends Biomater. Artif. Organs* (2008) 21(2):98-106.
Kirby, B. S. et al., "Acute Bronchospasm Due to Exposure to Polymethylmethacrylate Vapors During Percutaneous Vertebroplasty," *AJR* (2003) 180:543-544.
Koessler, M. J. et al., "Fat and Bone Marrow Embolism During Percutaneous Vertebroplasty," *Anesth. Analg.* (2003) 97:293-294.
Lidgren, L. "Bone Substitutes," *Karger Gazette* (2003) 65:1-4.
Derwent abstract of JP 1139516; Derwent week 198928.
English language abstract of EP 0 657 208 A1.
Machine translation of JP 1139516 (H06(1994)-0842898) from http://www4.ipdl.inpit.go.jp/Tokujitu/tjsogodbenk.ipdl last viewed on Jan. 22, 2009.

Nilsson, M. et al. "Biodegradation and biocompatability of a calcium sulphate-hydroxyapatite bone substitute," *J. of Bone & Joint Surgery* (Br) (2004) 86-B:120-125.
"Powder (substance)" entry from www.wikipedia.com, <<http://en.wikipedia.org/wiki/Powder_(substance)>> (last visited Dec. 1, 2008).
Notice of Allowance dated Apr. 25, 2008 in related U.S. Appl. No. 10/333,026.
Copending U.S. Appl. No. 12/122,873, filed May 19, 2008.
Copending U.S. Appl. No. 12/219,542, filed Jul. 23, 2008.
Copending U.S. Appl. No. 12/219,543, filed Jul. 23, 2008.
Cahn, R.W., ed. *Materials Science and Technology: A Comprehensive Treatment*, 1992, vol. 14, VCH, Weinheim, pp. 70-109.
Elliott, J. C. "Chapter 1: General Chemistry of the Calcium Orthophosphates," in *Structure and Chemistry of the Apatites and Other Calcium Orthophosphates*, 1994, Elsevier: Netherlands.
English language translation of JP 64-22256.
English language translation of JP 64-22257.
English language abstract of JP 5-168692 A.
English language translation of Jun. 2, 2009, Office Action in Japanese Application No. 2003-554244.
Office Action in copending U.S. Appl. No. 12/219,542 dated Jun. 19, 2009.
Office Action in copending U.S. Appl. No. 12/122,873 dated Jun. 19, 2009.
Office Action in copending U.S. Appl. No. 10/547,671 dated Aug. 5, 2009.
Bohner, M., "Physical and chemical aspects of calcium phosphates used in spinal surgery", Eur. Spine J. (2001) 10:S114-S121.
Barbalace, K. "Chemical Database: Calcium sulfate", Environmental Chemistry.com, 2009, 3 pages.
English language abstract of EP 0 657 208 Al.
English language abstract of JP 2000-000295 A.
English language abstract of JP 2001-106638 A.
English language translation of ES 2 178 556 A1, "Calcium sulfate cement capable of controlled biodegradation," (10 pgs.).
Eromosele et al., "Characterization and viscosity parameters of seed oils from wild plants," Science Direct: Bioresource Technology, 2002, 7 pages.
Nilsson et al., "The Effect of Aging an Injectable Bone Graft Substitute in Simulated Body Fluid," Key Engineering Materials, vols. 240-242 (2003), pp. 403-406.
Office Action in copending U.S. Appl. No. 10/257,561 dated Apr. 3, 2009.
Office Action in copending U.S. Appl. No. 10/257,561 dated Nov. 10, 2009.
Office Action in copending U.S. Appl. No. 10/578,734 dated Oct. 26, 2009.
Office Action in copending U.S. Appl. No. 12/122,873 dated Oct. 29, 2009.
Office Action in copending U.S. Appl. No. 12/219,542 dated Jan. 11, 2010.
Starling, S., "EFSA Says Calcium Sulphate Safe in Supplements," 2008, Nutraingredients.com, 4 pages.
Technical Specification, Calcium Sulfate Hemihydrate Food Grade, 2009, 1 page.
U.S. Appl. No. 12/911,198, filed Oct. 25, 2010.
U.S. Appl. No. 12/911,266, filed Oct. 25, 2010.
U.S. Appl. No. 13/613,563, filed Sep. 13, 2012.
Damien, C.J., et al., "Student Research Award in the Graduate Degree Candidate Category, 16th Annual Meeting of the Society for Biomaterials, Charleston, SC, May 20-23, 1990," *Journal of Biomedical Materials Research* (1990) 24:639-654.
De Robertis, A., et al., "Solubility of some calcium-carboxylic ligand complexes in aqueous solution" *Talanta* (1995) 42:1651-1662.
English language abstract of DE 202 16 632.
English language abstract of EP 1 002 513.
English language abstract of JP 2000-159564.
English language abstract of JP 2001-517997.
English language abstract of JP 2002-325831.
English language abstract of JP 2935708 B2.
English language translation of Japanese Office Action dated Jun. 1, 2010 in Japanese Application No. 2006-539432.

(56) References Cited

OTHER PUBLICATIONS

English language translation of Japanese Office Action dated Sep. 9, 2010 in Japanese Application No. 2006-507949.
English language translation of Japanese Office Action, dated Oct. 3, 2011, for Japanese Patent Application No. 2002-511972.
Gitelis, S. and Brebach, G. T., "The treatment of chronic osteomyelitis with a biodegradable antibiotic-impregnated implant," *J. Orthopaedic Surgery* (2002) 10(1):52-60.
Karr, J. C., "Management of a Diabetic Patient Presenting with Forefoot Osteomyelitis: The use of Cerament™ IBone Void Filler Impregnated with Vancomycin—An Off Label Use," *J. Diabetic Foot Complications* (2009) 1(4):94-100.
Lei, D., et al., "Mechanical properties of calcium sulphate/hydroxyapatite cement," *Bio-Medical Materials and Engineering* (2006) 16:423-428.
Machine Translation of JP-A-2002-058736.
Notice of Allowance in U.S. Appl. No. 10/257,561 dated Feb. 23, 2011.
Notice of Allowance in U.S. Appl. No. 10/547,671 dated Dec. 26, 2012.
Notice of Allowance in U.S. Appl. No. 10/578,734 dated Dec. 29, 2010.
Notice of Allowance in U.S. Appl. No. 10/578,734 dated Jul. 27, 2010.
Notice of Allowance in U.S. Appl. No. 11/587,313 dated Jan. 26, 2011.
Notice of Allowance in U.S. Appl. No. 12/585,194 dated Jun. 22, 2012.
Notice of Allowance in U.S. Appl. No. 12/585,194 dated Mar. 22, 2012.
Office Action and English language translation thereof for Japanese Patent Application 2001-574164, corresponding to U.S. Appl. No. 10/257,561 dated Feb. 2, 2011.
Office Action in U.S. Appl. No. 10/257,561 dated Apr. 27, 2010.
Office Action in U.S. Appl. No. 10/547,671 dated Aug. 16, 2010.
Office Action in U.S. Appl. No. 10/547,671 dated Aug. 23, 2011.
Office Action in U.S. Appl. No, 10/547,671 dated May 29, 2012.
Office Action in U.S. Appl. No. 10/547,671 dated May 5, 2010.
Office Action in U.S. Appl. No. 11/587,313 dated Jun. 18, 2010.
Office Action in U.S. Appl. No. 12/122,873 dated Feb. 27, 2012.
Office Action in U.S. Appl. No. 12/122,873 dated Mar. 19, 2010.
Office Action in U.S. Appl. No. 12/122,873 dated Sep. 8, 2010.
Office Action in U.S. Appl. No. 12/219,542 dated Jun. 25, 2010.
Office Action in U.S. Appl. No. 12/219,542 dated Mar. 1, 2012.
Office Action in U.S. Appl. No. 12/219,542 dated Oct. 18, 2010.
Office Action in U.S. Appl. No. 12/219,543 dated Feb. 27, 2012.
Office Action in U.S. Appl. No. 12/219,543 dated Mar. 19, 2010.
Office Action in U.S. Appl. No. 12/219,543 dated Sep. 8, 2010.
Office Action in U.S. Appl. No. 12/585,194 dated Aug. 11, 2011.
Office Action in U.S. Appl. No. 13/022,771 dated Nov. 14, 2012.
Parsons, J. R., et al., "Osteoconductive Composite Grouts for Orthopedic Use," *Annals New York Academy of Sciences* (1988) 523:190-207.
Richelsoph, K. C., et al., "Elution Behavior of Daptomycin-loaded Calcium Sulfate Pellets," *Clin. Orthopaedics and Related Res.* (2007) 461:68-73.
Singh, N. B. and Middendorf, B., "Calcium sulphate hemihydrate hydration leading to gypsum crystallization," *Prog. Crystal Growth & Characterization of Materials* (2007) 53:57-77.
Supplemental Notice of Allowance in U.S. Appl. No. 10/578,734 dated Sep. 17, 2010.

\* cited by examiner

BIORESORBABLE BONE MINERAL SUBSTITUTE COMPRISING WATER-SOLUBLE X-RAY CONTRAST AGENT

CROSS REFERENCE TO RELATED APPLICATIONS

This application is a national phase application based on PCT/SE02/02428, filed Dec. 20, 2002, the content of which is incorporated herein by reference, and claims the benefit of Sweden Application No. 0104359-5 filed Dec. 20, 2001 and the benefit of U.S. Provisional Application No. 60/341,282, filed on Dec. 20, 2001.

The invention refers to an artificial bone mineral substitute material as well as a composition for the same, which have improved radio-opacity. The invention also refers to the use of composition for an artificial bone mineral substitute material as an X-ray contrast medium.

The life expectancy of the world population has increased tremendously during the last 50 years. Our population is living longer than ever. The next ten years, it has been forecasted that there will be more people over 60 years of age than less than twenty years of age in Europe. More people will need medical help for diseases related to age, which will increase the pressure of the hospitals.

Bone is the second most common material to be transplanted after blood. The most reliable method to repair bone defects is to use autogenous bone, i.e. bone taken from another site in the body. Autografts are osteogenic, i.e. derived from or composed of any tissue which is concerned with the growth or repair of bone. However, problems may occur at the second surgical site where the graft is taken. To avoid this extra trauma allografts can be used, i.e. bone graft between individuals of the same species. Allografts have a lower osteogenic capacity than autografts and the rate of new bone formation might be lower. They also have a higher resorption rate, a larger immunogenic response and less revascularisation of the recipient. Allografts must also be controlled for viruses since they can transfer, for example, HIV and hepatitis. The use of allografts is now the most common method for bone transplantation and repairing of bone defects.

The problems with using autografts and the limited supply of bones at most hospitals has led to a lot of research in materials that can be used as bone substitutes. The ideal bone substitute should be biocompatible, injectable through a needle, self-setting, osteoconductive, resorbable and replaced by new normal bone.

An injectable bone graft substitute can improve the treatment of osteoporosis. Osteoporosis is a disease that acts upon older people. Bone is live tissue, new cells are formed and some cells die daily. In a year 10-30 % of our entire skeleton is remodeled. Osteoporosis leads to a total skeleton mass reduction because of a non-equilibrium state between cells that form bone (osteoblasts) and cells that resorb bone (osteoclasts). When the resorption rate of bone is higher than the rate of bone formation it leads to a total reduction of bone. The skeleton becomes weaker and finally a fracture occurs either by reason of a fall or just because the skeleton can not withstand the weight of the body. When the spine becomes weaker it will be curved and compressed.

Their are two types of bone: trabecular and cortical. The outside layer of bone usually consists of cortical bone, which is very dense and solid, trabecular bone is much more porous and is found inside of the bones. Osteoporosis initially effects the trabecular bone.

Fractures resulting from osteoporosis are very troublesome to treat. The skeleton is fragile and difficult to stabilise with screws and plates. Even if the screw insertion succeeds it often becomes loose when the patient later starts to move. To attach the screws to the bone a bone graft substitute can be injected in the drilled holes before screw insertion. The result is that the screw fixation improves and the patient recovers faster with less pain. If a thin layer of bone substitute is used it can be difficult to see in an X-ray picture. To improve the visibility, it could be possible to add a radiographic contrast medium to the material. To stabilise the spine, a bone graft substitute can be injected. If a bone substitute leaks from the spine, it will cause pressure on nearby tissues and nerves which will cause pain and eventually nerve injury.

One of the materials that has been used for stabilising the spine is the bone cement polymethylmethacrylate (PMMA). PMMA is a chain polymer that is glassy at room temperature. PMMA is a good material for intraocular lenses and hard contact lenses. It is also used to fixate the metal implant in hip joints and for skull defect reconstruction and vertebroplasty. PMMA is not resorbed in the bone. PMMA has a couple of drawbacks. For example PMMA cures with a strongly exothermic reaction, potentially damaging adjacent soft tissue structures i.e. cell death, particularly in the event of cement extrusion. Therefore, PMMA is not an optimal material for this indication.

Presently, mainly three kinds of bone substitutes are used for repairing bone: calcium phosphate, hydroxyapatite and calcium sulfate.

Calcium phosphates are suitable as bone substitutes because of their bioactive properties, i.e. having an effect on or obtaining response from living tissue. They have low fatigue properties relative to bone and can only be used in non-weight bearing areas. Their resorption rate is relatively slow, at least six months.

There are two different categories of calcium phosphates: CaP obtained by precipitation from an aqueous solution at room temperature (low-temperature CaP) and CaP obtained by a thermal reaction (high-temperature CaP). The calcium phosphates used in medicine are high-temperature CaP, for example α-tricalcium phosphate (α-TCP) and hydroxypatite (HA). Low-temperature CaP is used to synthesize high-temperature CaP.

Tricalcium phosphate ($Ca_3(PO_4)_2$) exists in two forms: α-TCP and β-TCP. The crystal structure of α-TCP is monoclinic and consists of columns of cations while the β-TCP has a rhombohedral structure. β-TCP is stable up to 1180° C. and α-TCP is stable between 1180-1470° C. α-TCP forms by heating β-TCP above 1180° C. and quenching it to retain its structure. α-TCP is less stable than β-TCP and forms the stiffer material calcium-deficient HA when mixed with water, see formula (1).

$$3\ Ca_3(PO_4)_2 + H_2O \rightarrow Ca_9(HPO_4)(PO_4)_5OH \quad (1)$$

Hydroxyapatite is the most stable calcium phosphate and the primary non-organic component of bone. Most of the bone graft substitutes on the market are made of hydroxyapatite. HA is highly crystalline and the least soluble of the calcium phosphates.

Hydroxyapatite and tri-calcium phosphate are the most common calcium phosphates used to fill bone defects and as implant coatings. They have low fatigue properties relative bone and can only be used in non-weight bearing areas. Their resorption rate is relatively slow, from six months to several years. It is possible to increase the rate of degradation slightly by increasing the surface area of the material, decreasing the crystallinity and the crystal perfection and decreasing the size of crystals and grains in the material. A higher resorption rate can be preferable to encourage bone formation.

Hydroxyapatite ($Ca_{10}(PO_4)_6(OH)_2$) is the major mineral component of bone. Artificial hydroxyapatite (HA) has a chemical and crystallographic structure similar to the natural HA of bone and has been studied as a bone replacement material for over 30 years. HA is highly crystalline and the most stable CaP in an aqueous solution. HA is the least soluble calcium phosphate at pH over 4.2, which means that other calcium phosphates with a pH over 4.2 will tend to dissolve and form precipitated HA. HA is biocompatible, not osteogenic but has osteoconductive properties. Most of the bone substitutes on the market are made of HA. They are regarded as degradable, but their degradation time is very long. The final compressive strength depends on which type of HA is used. If spray-dried HA is used the compressive strength is very low. Even the shape and size of the powder affect the mechanical strength.

There are several forms of HA that have been used experimentally and clinically: solid ceramic blocks, porous blocks and solid and porous particulate. The major use of HA is in the oral surgery, where the particulate HA is used. Particulate HA is inconvenient to use for orthopaedic applications because particles often migrate from the implant site before bone ingrowth secure them in place. Porous HA blocks have successfully been used for cranio-facial reconstructions and orthopaedic applications, but they are difficult to shape.

Research in calcium sulfates as a bone graft substitute has been carried out for more than a century. Several investigators have reported experiments using calcium sulfate hemihydrate, commonly known as Plaster of Paris (PoP). This material is well accepted by the body the resorption rate is faster than the rate of bone ingrowth and the mechanical strength for Plaster of Paris is low.

Calcium sulfate hemihydrate exists in two forms, α-form and β-form. The α-form has monoclinic structure and consists of compact, wellformed, and transparent large primary particles. The β-form has rhombohedral structure and consists of rugged secondary particles made up of extremely small crystals.

Plaster of Paris is made from calcium sulfate dihydrate (gypsum) through dehydration, see reaction (2.2). The gypsum is ground and heated until about 75% of the water is gone and $CaSO_4 \cdot \frac{1}{2}H_2O$ is obtained. When Plaster of Paris is mixed with water, an exothermic reaction takes place with gypsum as product, which is called rehydration of gypsum, see reaction (3). The structure of gypsum consists of layers of alternate $SO_4^{2-}$ ions strongly bonded to $Ca^{2+}$ and sheets of water molecules.

$$2(CaSO_4 \cdot 2H_2O) \xrightarrow{heat} 2(CaSO_4 \cdot \tfrac{1}{2}H_2O) + 3H_2O \quad (2)$$

$$2(CaSO_4 \cdot \tfrac{1}{2}H_2O) + 3H_2O \rightarrow 2(CaSO_4 \cdot 2H_2O) + heat \quad (3)$$

If calcium sulfate dihydrate is added to calcium sulfate hemihydrate the setting time will decrease because the nucleation time is eliminated. Crystal growing can start directly on the calcium sulfate dihydrate particles which thus act as an accelerator.

Disodium hydrogen phosphate ($Na_2HPO_4$) is used as an accelerator for the calcium phosphate compositions. When $Na_2HPO_4$ is added to the cement powder, the $(PO_4)^{3-}$ ions will bond to $Ca^{2+}$ ions and the precipitation rate will increase which gives a shorter setting time.

Research in the use of different radiocontrast materials in bone cement, i.e. PMMA, has been conducted and the influence of radiocontrast media in PMMA has been studied. The radiocontrast agents, bariumsulfate ($BaSO_4$) and zirconium dioxide ($ZrO_2$), are commonly added to polymethyl-methacrylite (PMMA) to ensure X-ray visibility and to ease radiological assessments. These two materials have negative side effects in that they may cause pathological bone resorption as well as cause damage to the articulating surface if they enter the joint space, a marked increase in the production of polyethylene wear debris being obtained. Furthermore, if included in bone substitutes, such an X-ray dense bone substitute may leak from the spine and cause nerve damages.

When such a ceramic bone is resorbed with time, it will subsequently contact other tissues. Contrast agents in the form of metals, zirconium oxide, or barium sulfate will remain at the site of treatment or will be spread as small particles to other organs, such as the lungs, and/or will ultimately be transported to the kidneys where they will be trapped. Thus, it is important that the contrast agent dissolves in the blood and is disposed of via the kidneys as primary urine.

Water soluble non-ionic X-ray contrast agents have been used in connection with polymeric materials. In WO 99/62570 such agents have been used for preventing the release of particles from the bone cement, i.e. the plastic material, which contribute to the wear of adjacent surfaces at the surgical site.

The object of this invention is to provide an artificial bone mineral substitute material, whereby the above-mentioned problems are eliminated or reduced.

Another object of the invention is to provide an artificial bone mineral substitute material which exhibits positive radiophysical effects in comparison with the state of the art.

Still another object is to provide a bone graft substitute which improves the possibility to detect leakage during the operation.

A further object of the invention is to provide a composition which after hardening results in a "safe" ceramic implant comprising a biocompatible X-ray contrast medium, whereby a leakage of the contrast agent from the site of injection is allowed, which does not give rise to inflammation in the vicinity of the site of injection and is thus atoxic for e.g. the nervous system.

Yet a further object is to provide a composition which does not exhibit the drawbacks of high viscosity at delivery and which provides improved Theological properties and allows injection at distant sites in comparison with the state of the art.

Still a further object of the invention is to provide a composition, whereby ceramic materials do not have to be included in the X-ray contrast medium.

Still another object of the invention is to provide a composition, whereby it is possible to follow the healing of bone defects and bone fractures.

Still yet a further object of the invention is to provide a composition which can be used in applications of bone defects communicating with joints.

These objects as well as other objects that will be apparent from the following description are accomplished by the artificial bone mineral substitute material as well as the composition for the same as claimed.

Figure 1:
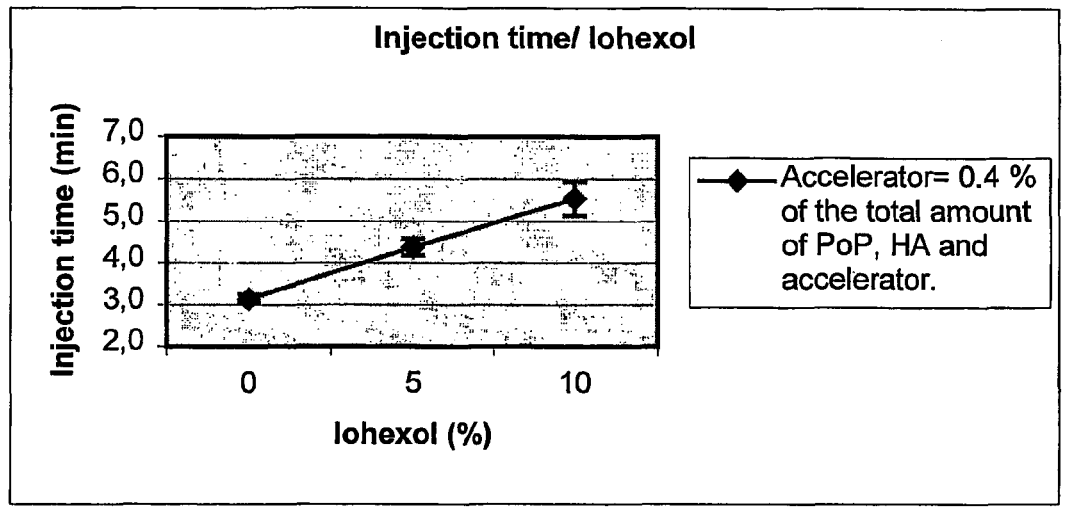
FIG. 1 shows the relation between injection time and amount of iohexol for a constant amount of accelerator for a calcium sulfate based composition.

The inventive composition as well as the inventive artificial bone mineral substitute material comprises at least one ceramic material and at least one water soluble non-ionic X-ray contrast agent. It is preferred that the composition is injectable and that the artificial bone obtained is bioresorbable.

Suitable conventional water soluble non-ionic X-ray contrast agents are iodinated aromatic compounds, which have one or several aromatic nuclei that are at least triiodo-substituted. Such agents are shown in U.S. Pat. No. 5,695,742 and comprise CAS (Chemical Abstract Service) registration numbers 31112-62-6 (metrizamide), 60166-93-0 (iopamidol), 78649-41-9 (iomeprol), 73334-07-3 (iopromide), 877771-40-2 (ioversol), 66108-95-0 (iohexol), 89797-00-2 (iopentol), 107793-72-6 (ioxilan), 99139-49-8 (II-1), 75751-89-2 (iogulamide), 63941-73-1 (ioglucol), 63941-74-2 (ioglucamide), 56562-79-9 (ioglunide), 76984-84-0 (MP-7011), 64965-50-0 (MP-7012), 77111-65-0 (MP-10007), 79944-49-3 (VA-7-88), 79944-51-7 (also shown in EP 033426), 79211-10-2 (iosimide), 79211-34-0 (iocibidol), 103876-29-5 (also shown in EP 0177414), 141660-63-1 (iofratol), 92339-11-2 (iodixanol), 79770-24-4 (iotrol), 71767-13-0 (iotasul), 81045-33-2 (iodecol), 143200-04-8 (also shown in WO 92/086), 143199-77-3 (also shown in WO 92/08691), 143200-00-4 (also shown in WO 92/08691), 78341-84-1 (also shown in U.S. Pat. No. 4,348,377),. 122731-47-9 (also shown in EP 0308364), 122731-49-1 (also shown in EP 0308364), 99139-65-8 (also shown in WO 85/01727), 99139-62-5 (also shown in WO 85/01727), and 78341-84-1 (also shown in EP 0023992).

Other such water soluble non-ionic X-ray contrast agents are shown in U.S. Pat. No. 5,447,711 and comprise iotrolan, ioxaglate, iodecimol, and iosarcol. Other suitable contrast agents are iotusal, ioxilane, and iofrotal.

Preferably, the water soluble non-ionic X-ray contrast agent has a low osmomolality such as iohexol, iodixanol, ioversol, iopamidol, and iotrolane.

For example, iohexol ($C_{19}H_{26}I_3N_3O_9$) as well as its dimer iodixanol can with advantage be used as a water soluble non-ionic X-ray contrast agent. These substances do not influence bone formation and they have a good biocompatibility in bone. They are used for different purposes in medicine. For example it can be used for patients with kidney failure to determine the rate of plasma clearance by the kidney.

Thus, the inventive composition as well as the inventive artificial bone mineral substitute material comprises at least one water soluble non-ionic X-ray contrast agent, preferably iohexol or its dimer iodixanol. When used in the inventive composition, the water soluble non-ionic X-ray contrast agent should have a concentration between 2 and 20 weight % of the total weight of the powder components in the same.

Of course, other contrast agents can also be included in the inventive artificial bone mineral substitute material as well as the composition for the same.

Suitable ceramics are calcium sulfates and calcium phosphates.

Examples of calcium phosphate ceramics are α-tricalcium phosphate, hydroxyapatite, dicalcium phosphate dihydrate, anhydrous dicalcium phosphate, tetracalcium phosphate, β-tricalcium phosphate, calcium-deficient hydroxyapatite, monocalcium phosphate monohydrate, mono-calcium phosphate, calcium pyrophosphate, precipitated hydroxyapatite, carbonated apatite (dahlite), octocalcium phosphate, amorphous calcium phosphate, oxyapatite, and carbonatoapatite.

Suitable types of calcium phosphates are shown in Table 1 below.

| Ca/P | Calcium phosphate | Formula |
|---|---|---|
| 1.35 | Amorphous calcium phosphate I ACP | — |
| 1.35 | Amorphous calcium phosphate II ACP | — |
| 0.5 | Monocalcium phosphate monohydrate MCPM | $Ca(H_2PO_4)_2.2H_2O$ |
| 1.0 | Dicalcium phosphate dihydrate DCPD (brushite) | $CaHPO_4.2H_2O$ |
| 1.33 | Octacalcium phosphate | $Ca_8(HPO_4)_2(PO_4)_4.5H_2O$ |
| 1.5 | Calcium deficient hydroxyapatite (CDHA) | $Ca_9(HPO_4)(PO_4)_5(OH)$ |
| 1.5 | Tricalcium phosphate (TCP) | $Ca_3(PO_4)_2$ |
| 1.67 | Hydoxyapatite (HA) | $Ca_{10}(PO_4)_6(OH)_2$ |

Preferably, the calcium phosphate has a Ca/P-ratio between 0.5 and 2. Likewise, it is preferred that the particulate calcium phosphate is hydroxyapatite (HA), tri-calcium-phosphate (TCP), or a mixture thereof.

In the composition the particulate calcium phosphate should have a particle size of less than 20 μm, preferably less than 10 μm.

The calcium sulfate can be calcium sulfate α-hemihydrate, calcium sulfate β-hemihydrate, or calcium sulfate β-dihydrate.

Calcium carbonate can also be used as a ceramic.

The inventive composition for an artificial bone mineral substitute material can in itself be used as an X-ray contrast medium. An additive X-ray effect is obtained by means of the composition according to the invention, since the X-ray contrast ability of its ceramic component is utilized. The inclusion of at least one water soluble non-ionic X-ray contrast agent in the composition increases the original X-ray density of the X-ray dense bone substitute. Thus, no further ceramic radio contrast agents, such as bariumsulfate and zirconium dioxide, have to be included in the composition for an artificial bone mineral substitute material according to the invention. Such hard ceramic particles will wear joints when torn off from the bone substitute. In the joints they will cause physical damage and eventually result in inflammatory reactions.

Thus, the inventive composition, which comprises at least one water soluble non-ionic X-ray contrast agent, can be injected adjacent to joints, and the resulting artificial bone mineral substitute material can be used for bone defects communicating with joints. Such applications include the repair of osteochondral joints defects as well as fractures or bone defects involving a joint.

In addition, the dual origin of X-ray density can be further exploited, for example in order to follow the healing process after implantation of the inventive composition in a human or animal body. When the obtained artificial bone mineral substitute material, which comprises at least one water soluble non-ionic X-ray contrast agent, is replaced by ingrowing bone, the water soluble agent will slowly disappear. This results in a progressive decline in X-ray density, which can be monitored.

In order to increase the healing process the inventive composition should also comprise at least one osteogenic factor. In this connection an osteogenic factor is a substance that influences bone turnover, either by increasing bone formation or by decreasing bone breakdown.

Suitable bone inducing (stimulating and/or accelerating) substances are growth factors and hormones. Growth factors and derivatives thereof are preferred, which are locally acting, e.g. the BMP family (Bone Morphogenetic Proteins). It is also preferred to use autologous growth factors in order to accelerate bone growth.

Examples of such bone stimulating compounds are parathyorid hormones and derivatives thereof, estrogenes, progesterones, androgenes, testosterones, calcitonin, somatomedin, and oxytocin.

The enamel matrix proteins amelin-1, amelin-2 and ameloblastin as well as the cholesterol-lowering compound statin can also be included in order to induce, stimulate and/or accelerate bone formation.

Examples of suitable bone breakdown inhibitors are biphosphonates, osteocalcin, osteonectin and derivates thereof, which can be included in the inventive composition and the resulting material.

The inventive composition may also include at least one accelerator, which preferably is calcium sulfate di-hydrate and/or disodium hydrogen phosphate. When calcium sulfate dihydrate is used, it should have a concentration between 0.1 and 10 weight % of the total weight of the powder components in the composition.

A preferred injectable composition comprises particulate calcium sulfate hemihydrate, particulate calcium phosphate. The composition may also include particulate calcium sulfate dihydrate as an accelerator and optionally vitamin E. When vitamin E is included, it should have a concentration between 0.1 and 10 weight % of the total weight of the powder components in the composition.

Likewise, the inventive composition as well as the resulting artificial bone mineral substitute material may further include kalciferols, kalcitriols, as well as other D vitamins and derivates thereof. These compounds help to regulate calcium metabolism and normal calcification of the bones in the body as well as influence the utilization of mineral phosphorus.

Compounds with static or cidal effects against invading foreign living material can also be included. Such compounds include natural antiobiotics as well as other semisynthetic and synthetic antibacterial compounds, antiviral compounds, antifungal compounds, and antiparasite compounds.

Cytostatics and other chemotherapy substances can also be included in the composition as well as the material according to the invention.

When at least one powdered ceramic is a calcium sulfate hemihydrate and at least one of hydroxyapatite and β-tricalcium phosphate, the at least one of hydroxyapatite and β-tricalcium phosphate has a concentration between 20 and 60 weight % of the total weight of the powder components in the inventive composition.

When at least one powdered ceramic is a calcium sulfate hemihydrate and α-tricalcium phosphate, the calcium sulfate hemihydrate has a concentration between 1 and 30 weight % and the α-tricalcium phosphate has a concentration between 50 and 99 weight % of the total weight of the powder components in the inventive composition, respectively Other injectable compositions for an artificial bone mineral substitute material are similarly based on tetracalciumphosphate (TTCP) and hydroxyapatite (HA); α-tricalcium phosphate (TCP) and tetracalciumphosphate; α-tricalcium phosphate, tetracalciumphosphate, and citric acid; α-tricalcium phosphate, tetracalciumphosphate, dicalcium sulfate dihydrate (DCPD), and hydroxyapatite; α-tricalcium phosphate, dicalcium phosphate (DCP), calcium carbonate, and hydroxyapatite; and hydroxyapatite acrylic monomers.

By including a water-soluble non-ionic X-ray contrast agent the strength of the bone mineral substitute is somewhat decreased. This can, however, be compensated by reducing the water content thereof. Nevertheless, the inventive artificial bone mineral substitute material is preferably used in connection with indications, in which a high strength is not required but when a high X-ray contrast is required.

An additional advantage of the artificial bone mineral substitute material according to the invention is that the water soluble non-ionic X-ray contrast agent also functions effectively in its solid dry state. Thus, the water-soluble non-ionic X-ray contrast agent is mixed into the inventive composition as well as the inventive artificial bone mineral substitute material and is evenly distributed in the same.

Preferably, the water soluble non-ionic X-ray contrast agent is mixed into the dry sulfate component as a dry powder, or it is dissolved in the aqueous liquid of the composition. It is also preferred that the aqueous liquid component is distilled water.

In the composition according to the invention a ratio between the powder components and the aqueous liquid component, i.e. the liquid/powder ratio, should be between 0.1 and 0.4 ml/g.

In a preferred embodiment of the inventive injectable composition, which comprises calcium sulfate hemihydrate, calcium phosphate, and an aqueous liquid, the water is allowed to react with the dry sulfate or phosphate components of the composition. This results in a crystallization of the ceramic component(s).

When the artificial bone mineral substitute material is resorbed in the body, the water in the blood will ultimately dissolve the sulfate ceramic and the water soluble non-ionic X-ray contrast agent will be released and disposed of.

Likewise, in a mixture of sulfate/phosphate or sulfate/hydroxyapatite, the water soluble non-ionic X-ray contrast agent will be dissolved in a more limited extent since it will be locked within the bone mineral substitute material.

For example, a composite of hydroxyapatite and calcium sulfate results in a material with much better handling properties than hydroxyapatite alone. The mixture can be injected or manually inserted to a bone defect under pressure. The hydroxyapatite particles are held in place by the Plaster of Paris which initially acts as a binder. When the Plaster of Paris resorbs, a matrix with controlled porosity is obtained, which supports bone ingrowth. If the amount of hydroxyapatite is at least 40%, the temperature of the setting reaction is decreased which is another reason for adding hydroxyapatite to Plaster of Paris.

Thus, by mixing the water soluble non-ionic X-ray contrast agent as a powder in the dry sulfate or phosphate component, respectively, the dissolution of the same with time can be controlled.

The very viscous bone substrate is more easily injected than those according to the state of the art, i.e. positive Theological properties are obtained when a water soluble non-ionic X-ray contrast agent is included in the composition for a bone mineral substitute material.

EXAMPLES

The invention will now be further described and illustrated by reference to the following examples. It should be noted, however, that these examples should not be construed as limiting the invention in any way.

Example 1

X-ray Analysis

The X-ray visibility was determined with three different amounts of iohexol in both calcium phosphate and calcium sulfate based compositions. Two different tests were performed. In one test the samples used for setting tests were subjected to X-rays and the visibility of the three samples were compared. Four samples of each material were studied. The liquid/powder ratio was the same for the three tests. In the other test, holes were drilled in bovine vertebrae. The holes were 10 mm in diameter and the depth was 10 mm. The holes were filled with material by injection through a syringe and analysed by X-ray. The visibility of the different materials was compared with the visibility of bone. The X-ray settings were 60 kV and 40 mAs. The same equipment was used for both tests. Table 2 shows the compositions based on calcium sulfate hemihydrate, and in Table 3 the compositions based on calcium phosphate are shown. An aluminium ladder scaled from 1-5 was used for the comparison, 5 being the lowest visibility and 1 the highest.

TABLE 2

| Iohexol (wt %) | PoP (wt %) | HA (wt %) | Accelerator (wt %) | Liquid/powder ratio |
|---|---|---|---|---|
| 10 | 53.28 | 36 | 0.72 | 0.21 |
| 5 | 56.24 | 38 | 0.76 | 0.21 |
| 0 | 59.2 | 40 | 0.8 | 0.21 |

TABLE 3

| Iohexol (wt %) | TCP (wt %) | PoP (wt %) | Calcium sulfate dihydrate (wt %) | Liquid/powder ratio |
|---|---|---|---|---|
| 10 | 70 | 19.8 | 0.2 | 0.28 |
| 5 | 75 | 19.8 | 0.2 | 0.28 |
| 0 | 80 | 19.8 | 0.2 | 0.28 |

It was found that the X-ray visibility was improved by adding a radio-contrast medium, such as iohexol or its dimer iodixanol. A concentration of 10% iohexol makes the visibility significantly better both in calcium phosphates and calcium sulfates compared to bone. There is no difference between the visibility in calcium phosphates and calcium sulfates.

Example 2

Test of Injectability

An Instron 8511.20 equipment was used. Twenty gram of each powder was mixed with distilled water and added to a 10 ml syringe with a 2 mm diameter opening. The syringe was placed in the Instron machine and compressed at a constant rate of 10 mm/min. For injection of the paste by hand, the maximum force corresponds to about 120 N. The Injection time was calculated as the time from start mixing powder and liquid until the force is more than 120 N. The final value for the injection time was taken as a mean value of six tests. For clinical applications, the required injection time is 3 to 8 minutes.

The use of the inventive composition for an artificial bone mineral substitute material as an injectable X-ray contrast medium was tested. Three samples of a contrast medium with or without a water soluble non-ionic X-ray contrast agent were tested, the total injection time as well as the weight extruded from syringe being measured. The results are shown in Table 4 below.

TABLE 4

| Contrast medium | Total injection time (min) | Weight extruded from syringe (%) |
|---|---|---|
| Water (deionized) L/P = 0.28 Sample | | |
| 1 | 4.23 | 22 |
| 2 | 4.17 | 20 |
| 3 | 4.28 | 16 |
| Iohexol 10.0% L/P = 0.326 $H_2O$/P = 0.28 Sample | | |
| 1 | 6.28 | 77 |
| 2 | 6.77 | 68 |
| 3 | 6.78 | 69 |

The utility, i.e. the injectability, of the contrast medium is markedly increased after the inclusion of the water soluble non-ionic X-ray contrast agent.

Further material compositions tested for injection time are shown in Table 5 and 6. In Table 5 the composition based on calcium sulfate hemihydrate are shown, which were tested for in injection time tests. Table 6 shows the corresponding compositions based on calcium phosphate.

TABLE 5

| Iohexol (wt %) | PoP (wt %) | HA (wt %) | Accel. (wt %) | Liquid/powder ratio |
|---|---|---|---|---|
| 10 | 53.64 | 36 | 0.36 | 0.21 |
| 10 | 53.28 | 36 | 0.72 | 0.21 |
| 10 | 52.92 | 36 | 1.08 | 0.21 |
| 5 | 56.62 | 38 | 0.38 | 0.21 |
| 0 | 59.6 | 40 | 0.4 | 0.21 |

TABLE 6

| Iohexol (wt %) | α-TCP (wt %) | PoP (wt %) | Calcium sulfate dihydrate (wt %) | Liquid/powder ratio |
|---|---|---|---|---|
| 10 | 70 | 19.8 | 0.2 | 0.26 |
| 5 | 75 | 19.8 | 0.2 | 0.26 |
| 0 | 80 | 19.8 | 0.2 | 0.26 |

With calcium sulfate hemihydrate as a ceramic the injection time was found to be dependent on the amount of iohexol or its dimer iodixanol. The influence of iohexol was investigated in the same way, 0, 5 and 10% of johexol were tested with a constant amount of accelerator. The tests showed that an increase in amount of iohexol increases the injection time, see FIG. 1.

Figure 2:
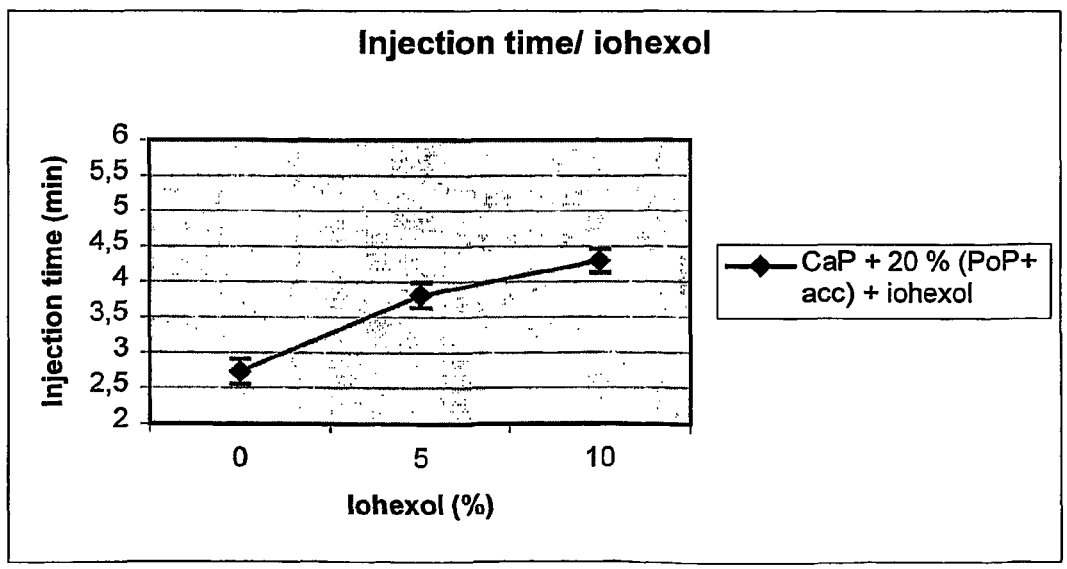
FIG. 2 shows the relation between injection time and amount of iohexol for calcium phosphate based compounds.

In addition, iohexol increases the injection time when calcium phosohate is used as a ceramic, see FIG. 2.

Example 3

Test of Setting

To determine the time of setting the ASTM standard test method by Gilimore needles has been used. The Gullmore apparatus consists of two needles with different weights applied. The initial needle has a diameter of 2.12±0.05 mm and a weight of 113±0.5 g is applied. The final needle has a diameter of 1.06±0.05 mm and a weight of 453.6±0.5 g.

To prepare test specimens the iohexol is first dissolved in distilled water and then added to the powder mixture. 10 gram of powder, with the iohexol included was used in each test. After mixing the paste is put into two moulds to form the test specimens. The initial and final setting time was taken as a mean value of the two tests. This procedure was repeated six times. The result presented is the mean value of the six tests.

The initial setting time is the time from the moment water is added to the bone substitute powder until the initial needle leaves no mark on the surface of the specimen. The final setting time is the time required for the paste to set so much that the final needle leaves no mark on the surface.

The ultimate amount of HA is 40 wt % if a mixture of PoP, HA and accelerator is used. Therefore the amount of HA is related to PoP and the accelerator. When materials with 0, 5, 10 wt % of iohexol were tested the iohexol was first calculated and then 40% HA and for example 0,4 wt % accelerator and 59.6 wt % PoP of the rest were used. The compositions of the tested materials are shown in Table 7.

TABLE 7

| Iohexol (wt %) | PoP (wt %) | HA (wt %) | Accel. (wt %) | Liquid/powder ratio |
|---|---|---|---|---|
| 10 | 53.64 | 36 | 0.36 | 0.21/0.19/0.17 |
| 10 | 53.28 | 36 | 0.72 | 0.21 |
| 10 | 52.92 | 36 | 1.08 | 0.21 |
| 5 | 56.62 | 38 | 0.38 | 0.21 |
| 5 | 56.24 | 38 | 0.76 | 0.21 |
| 5 | 55.86 | 38 | 1.14 | 0.21 |
| 0 | 59.6 | 40 | 0.4 | 0.21 |
| 0 | 59.2 | 40 | 0.8 | 0.21 |
| 0 | 58.8 | 40 | 1.2 | 0.21 |

The final setting time for calcium sulfate hemihydrate and calcium phosphate based bone substitutes should preferably be less than 15 minutes.

It was found that the setting time is dependent on amount iohexol; an adding iohexol to calcium sulfate hemihydrate compositions increases the setting time. Furthermore, the setting time decreases with increased amount of accelerator.

The results of the setting test with different amounts of accelerator and iohexol as in Table 7 with a liquid/powder ratio of 0.21 are shown in Table 8 below.

TABLE 8

| Iohexol (wt %) | Accel. (wt %) | Initial setting time (min) | Final setting time (min) |
|---|---|---|---|
| 10 | 0.36 | 6.8 ± 0.5 | 13.4 ± 0.6 |
| 10 | 0.72 | 5.8 ± 0.2 | 12.9 ± 0.4 |
| 10 | 1.08 | 5.5 ± 0.3 | 12.7 ± 0.5 |
| 5 | 0.38 | 5.4 ± 0.2 | 11.2 ± 0.4 |
| 5 | 0.76 | 5.0 ± 0.5 | 10.2 ± 0.4 |
| 5 | 1.14 | 4.6 ± 0.2 | 9.3 ± 0.8 |
| 0 | 0.4 | 4.9 ± 0.3 | 9.0 ± 0.5 |
| 0 | 0.8 | 4.0 ± 0.3 | 7.2 ± 0.4 |
| 0 | 1.2 | 3.3 ± 0.1 | 6.1 ± 0.4 |

Figure 3:
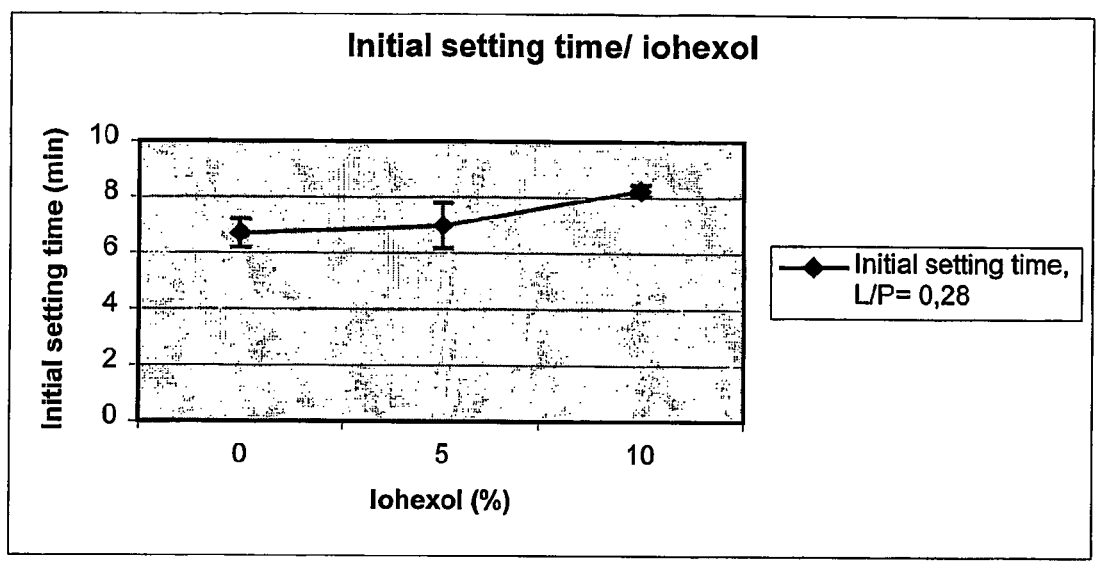
FIG. 3 shows the relation between setting time and amount of iohexol for a calcium phosphate compound with a liquid/powder ratio of 0.28.

Even for calcium phosphates the setting time is increased if iohexol is added. The more iohexol the longer becomes the setting time, see FIG. 3.

Example 4

Compression Test

The compressive strength is the maximum load a material can withstand without breaking. An Instron 8511.20 mechanical test machine was used for determining the compressive strength.

Paste from mixed powder and distilled water was injected to a PTFE mould. 16 cylindrical samples with a diameter of 4 mm and a height of about 8 mm were made. Calcium phosphate samples were stored in 0.9% saline solution at a temperature of 37° C. for 14 days before testing, while the samples of mixtures with calcium sulfate were stored in air for 48 hours.

The samples were compressed vertically in the Instron machine at a rate of 1 mm/min until they cracked. The compressive strength C, was calculated as C=F/A, where F=Force (N) and A=cross section area ($m^2$). The maximum force was used as F.

It was found that the compression strength is not dependent of the amount of accelerator and the compressive strength of a calcium phosphate ceramic decreased when iohexol was added.

Example 5

Density Testing

The absorption of material in saline solution was investigated for calcium phosphate containing different amounts of iohexol or its dimer iodixanol. Materials containing iohexol or its dimer iodixanol had a lower density after 14 days than materials without the same. This means that these compounds are absorbed in the water and the porosity increases if either of them is added, a higher porosity can promote bone ingrowth.

Example 6

Scanning Electron Microscope Analysis

For the calcium sulfate based compositions it was impossible to see any difference in the structure if iohexol is added.

The most important benefit with adding iohexol or its dimer iodixanol to calcium sulfates and calcium phosphates is the improved X-ray visibility. For example, adding 10% iohexol can increase the chance of detecting any leakage when injected to the spine or hip, or at other locations. Complications can be avoided in this fashion. The increased injection time will make the injection easier and give the surgeon more time to work. The increased setting time is no problem because of the possibility to control it with changing the liquid/powder ratio or the amount of accelerator.

The invention claimed is:

1. An artificial bone mineral substitute material prepared from powder and aqueous components, the artificial bone mineral substitute material being bioresorbable and comprising from 52.92 wt % to 59.6 wt % of calcium sulfate hemihydrate relative to the total weight of the powder components, from 36 wt % to 40 wt % of hydroxyapatite relative to the total weight of the powder components, a water soluble non-ionic X-ray contrast agent, an accelerator, which is calcium sulfate dihydrate, and an aqueous liquid, wherein said bone mineral substitute material does not include polymethylmethacrylate (PMMA).

2. The artificial bone mineral substitute material of claim 1, wherein the water soluble non-ionic X-ray contrast agent is chosen from iohexol, ioversol, iopamidol, iotrolane, iodixanol, metrizamide, iodecimol, loglucol, ioglucamide, ioglunide, iogulamide, iomeprol, iopentol, iopromide, iosarcol, iosimide, iotusal, ioxilane, iofrotal, and iodecol.

3. The artificial bone mineral substitute material of claim 1, wherein the water soluble non-ionic X-ray contrast agent is iohexol.

4. The artificial bone mineral substitute material of claim 1, which further comprises at least one osteogenic factor.

5. The artificial bone mineral substitute material of claim 1, which further comprises vitamin E.

6. The artificial bone mineral substitute material of claim 1, wherein said calcium sulfate hemihydrate is calcium sulfate α-hemihydrate.

7. The artificial bone mineral substitute material of claim 1, wherein the calcium sulfate dihydrate is present in an amount from 0.1 wt % to 10 weight % relative to the total weight of the powder components.

8. The artificial bone mineral substitute material of claim 1, wherein the aqueous liquid is distilled water.

9. The artificial bone mineral substitute material of claim 1, wherein the powder components and the aqueous liquid are present in a liquid/powder ratio between 0.1 ml/g and 0.4 ml/g.

10. An artificial bone mineral substitute material prepared from powder and aqueous components, the artificial bone mineral substitute material being bioresorbable and comprising 59.6 wt % of calcium sulfate hemihydrate relative to the total weight of the powder components, 40 wt % of hydroxyapatite relative to the total weight of the powder components, iohexol, an accelerator, which is calcium sulfate dihydrate, and an aqueous liquid, wherein said bone mineral substitute material does not include polymethylmethacrylate (PMMA).

* * * * *